US006471955B1

(12) United States Patent
Tremont et al.

(10) Patent No.: US 6,471,955 B1
(45) Date of Patent: Oct. 29, 2002

(54) PH-SELECTIVE DELIVERY SYSTEM USING CROSSLINKED POLYMERIC RESINS AS VEHICLES

(75) Inventors: Samuel J. Tremont, Manchester; Denis Forster, Ladue, both of MO (US); Ricky L. Fenton, Collinsville, IL (US); Yinong Ma, Westfield, MA (US)

(73) Assignee: Pharmacia Corporation, St. Louis, MO (US)

( * ) Notice: Subject to any disclaimer, the term of this patent is extended or adjusted under 35 U.S.C. 154(b) by 0 days.

(21) Appl. No.: 09/050,042

(22) Filed: Mar. 30, 1998

Related U.S. Application Data

(60) Provisional application No. 60/042,642, filed on Apr. 4, 1997.

(51) Int. Cl.[7] ............ A61K 31/75; A61K 31/231; A61P 1/04
(52) U.S. Cl. ............ 424/78.18; 514/690; 514/729; 514/926; 514/927
(58) Field of Search .............. 424/486, 78.18; 530/816; 525/54.1, 54.11; 514/690, 729, 925–27

(56) References Cited

U.S. PATENT DOCUMENTS

| | | | | |
|---|---|---|---|---|
| 4,228,152 A | | 10/1980 | Ferruti et al. ........... 424/81 |
| 4,273,873 A | * | 6/1981 | Sugitachi et al. | |
| 4,615,697 A | | 10/1986 | Robinson ............. 604/890 |
| 4,663,308 A | | 5/1987 | Saffran et al. ........... 514/3 |
| 4,921,707 A | | 5/1990 | Racz et al. ............ 424/690 |
| 5,169,640 A | | 12/1992 | France et al. ............ 424/470 |
| 5,275,824 A | | 1/1994 | Carli et al. ............ 424/490 |
| 5,474,767 A | | 12/1995 | Tremont ............ 424/78.27 |
| 5,607,691 A | | 3/1997 | Hale et al. ............ 424/449 |
| 5,723,320 A | * | 3/1998 | Dehlinger | |
| 5,783,214 A | | 7/1998 | Royer ............ 424/499 |
| 5,821,343 A | * | 10/1998 | Keogh | |
| 5,827,925 A | | 10/1998 | Tremont et al. ........ 525/102 |
| 5,840,674 A | | 11/1998 | Yatvin et al. ............ 514/2 |

FOREIGN PATENT DOCUMENTS

| | | | | |
|---|---|---|---|---|
| WO | 92/01477 | 2/1992 | ........ A61K/47/48 |
| WO | 95/28916 | 11/1995 | ........ A61K/9/16 |

OTHER PUBLICATIONS

J. Sarobe et al.: "Nephelometric Assay of Immunoglobulin G Chemically Bound to Chloromethyl Styrene Beads", Polymers for Advanced Technologies, vol. 7, No. 9, (Sept. 1, 1996) pp. 749–753.

(List continued on next page.)

*Primary Examiner*—Edward J. Webman
(74) *Attorney, Agent, or Firm*—Fitzpatrick, Cella, Harper & Scinto

(57) ABSTRACT

This invention provides a method of preparing a polymeric delivery system for active ingredients having enhanced site specific release performance characteristics. The delivery system is formed either by attaching the active ingredient to a linker through an acid-sensitive covalent bond, then forming a covalent bond between the linker and a portion of the subunits of a crosslinked polystyrene polymer, or by attaching a linker to a portion of the subunits of a crosslinked polystyrene polymer, then attaching the active ingredient to the polymer-linker combination through an acid-sensitive covalent bond. The invention also provides a delivery system comprising an active ingredient covalently bonded through an acid-sensitive covalent bond to a linker, which is in turn covalently bonded to a portion of subunits of a crosslinked polystyrene polymer. The invention further provides a method for treatment or prevention of gastric ulcers using a delivery system capable of delivering prostaglandin or prostacyclin drugs, especially misoprostol.

13 Claims, 1 Drawing Sheet

OTHER PUBLICATIONS

P.A. Parsons–Wingerter: "Cooperativity in Hepatocyte Culture from Cell–Cell and Cell–Substrate Interactions", Dissertation Abstracts International, vol. 54, No. 1, p. 368 (1993).

E.C. Blossey et al.: "Synthesis Reactions and Carbon–13 Ft NMR Spectroscopy of Polymer–Bound Steroids", J. Org. Chem., vol. 55, No. 15, pp. 4664–4668 (1990).

C. Larsen et al.: "Macromolecular Prodrugs", Acta Pharm. Suec., vol. 25, No. 1 (1988) pp. 1–14.

E. Teslariu et al.: "The Investigations on Some Pharmacokinetic Properties of Metronidazole Bound on Polymeric Support", Biopharm. Pharm. Technol., 1st, pp. 903–904.

S. Dumitriu et al.: Bioactive Polymers, Chim. Oggi, No.9 (Sep. 1988) pp. 59–63.

J. Kopecek, et al., Journal Of Controlled Release, vol. 19, (1992), p. 121.

S. Tremont, et al., Journal Of Medicinal Chemistry, vol. 36, (1993), p. 3087.

P. Yeh, et al., Journal Of Controlled Release, vol. 36, (1995), p. 109.

A. Bilia, et al., International Journal Of Pharmacy, vol. 130, (1996), p. 83.

I. Kim, et al., Archives Of Pharmacal Research, vol. 19, (1996), p. 18.

C. Ebert, et al., "The Antiplatelet Activity Of Immobilized Prostacyclin", Journal Of Biomedical Materials Research, vol. 16, No. 5, (1982), pp. 629–638.

* cited by examiner

US 6,471,955 B1

PH-SELECTIVE DELIVERY SYSTEM USING CROSSLINKED POLYMERIC RESINS AS VEHICLES

This application claims the benefit of U.S. Provisional Application No. 60/042,642, filed Apr. 4, 1997.

BACKGROUND OF THE INVENTION

1. Field of the Invention

This invention relates to a method for preparing a delivery system for an active ingredient by attaching the active ingredient to a linker through an acid-sensitive covalent bond, and attaching the linker to a portion of the subunits of a crosslinked polystyrene polymer. The invention also relates to a delivery system comprising an active ingredient covalently bonded through an acid-sensitive covalent bond to a linker, which is in turn covalently bonded to a portion of subunits of a crosslinked polystyrene polymer. The invention is further related to a method for treatment or prevention of gastric ulcers by administering a delivery system capable of delivering prostaglandin or prostacyclin drugs, especially misoprostol.

2. Related Background Art

Polymeric materials are frequently used to achieve controlled oral delivery of drugs. In most controlled-release devices, the drug molecule is not covalently bonded to the polymer, which acts merely as a barrier or as a reservoir from which the drug diffuses. The diffusion is often controlled by the degree of swelling of the polymer matrix on contact with aqueous media, as in the systems described in U.S. Pat. Nos. 5,275,824; 5,169,640; 4,921,707; 4,615,697; and in PCT Application WO 95/28916. However, some controlled-release systems are pH-selective, allowing release of the drug only within a specified pH range.

An example of pH-selective delivery can be found in polymeric systems consisting of interpenetrating networks of polyethylene glycol and polyacrylic acid. Such systems are disclosed in the International Journal of Pharmacy, Vol. 130, page 83 (1996) and in Archives of Pharmacal Research, Vol. 19, page 18 (1996). The polymeric network of these systems does not swell at gastric pH, but does swell on contact with the higher pH of the intestines, allowing release of the drug in the intestines. The swelling is believed to be due to deprotonation of the acrylic acid functional groups at the higher pH.

A delivery system to accomplish selective delivery to a particular site in the body is described in U.S. Pat. No. 4,663,308. In this system, a polymer which is crosslinked with a compound containing azo bonds is used as a coating for the drug substance. These azo bonds are reduced by enzymes in the large intestine, leading to cleavage of the crosslinks, causing the olymer coating to disintegrate, thereby releasing the rug in the large intestine.

Systems similar to the one described in U.S. Patent No. 4,663,308 are described in the Journal of Controlled Release: Vol. 19, page 121 (1992); and Vol. 36, page 109 (1995). The polymers employed in these systems do not swell at the typical gastric pH value of from 1 to 4, but pass unchanged into the intestine, where the higher pH value causes the polymer matrix to swell. The swelling allows enzymes in the intestine to enter the polymer and break the azo crosslinks in the polymer matrix, which in turn allows the drug to diffuse through the uncrosslinked polymer matrix.

None of the aforementioned controlled-release systems contains a drug which is covalently bonded to the polymer matrix. U.S. Pat. No. 4,228,152 describes a prostaglandin delivery system in which the prostaglandin molecule is covalently bonded to a polyacrylate or polymethacrylate chain directly, or indirectly through an oxyalkylenic, aminoalkylenic, or oxyaminoalkylenic chain. Release of the prostaglandin is effected by the gradual hydrolysis of the bonds connecting the prostaglandin to the polymer matrix. No suggestion is made either that the release is selective with regard to pH, or that the release is targeted to a particular site in the body.

A delivery system in which a covalently-bonded drug is selectively released at a predetermined pH is described in PCT Application No. WO 92/01477; U.S. Pat. No. 5,474,767; and Journal of Medicinal Chemistry, Vol. 36, p. 3087 (1993). In these references, pH-selective drug delivery systems comprise a drug covalently bonded to a linker by reaction with a silyl chloride functional group on the linker, thus forming an acid-sensitive silyl ether bond, and a polymer which is covalently bonded to the linker-drug combination. The polymer is crosslinked following bonding of the linker, or in some cases, prior to bonding of the linker. The exemplified preferred polymer in the inventions of WO 92/01477 and U.S. Pat. No. 5,474,767 is a polybutadiene containing amine functional groups. The invention of U.S. Pat. No. 5,474,767 is limited to polymers derived from non-aromatic unsaturated monomers. Other suitable polymers described in WO 92/01477 are polyamines, polybutadienes, copolymers of 1,3-dienes, polysaccharides, hydroxypropylmethylcellulose, amino-celluloses and proteins, e.g., chitosan, and polymers of acrylic and methacrylic acids, maleic copolymers thereof, and polymers having derivatizable olefinic bonds. While the pH-sensitive site-specific delivery systems of these references provide an excellent means of site specific drug delivery, polymeric pH-sensitive site-specific delivery systems having improved drug release performance characteristics would be highly advantageous.

SUMMARY OF THE INVENTION

This invention provides a method of preparing a polymeric delivery system for an active ingredient having enhanced site-specific release performance characteristics. The delivery system is formed either by attaching the active ingredient to a linker through an acid-sensitive covalent bond formed between a hydroxyl, $CO_2H$, amino, mercapto, or enolizable carbonyl substituent on the active ingredient and a reactive group on the linker, and then attaching the linker to a portion of the subunits of a crosslinked polystyrene polymer through a linker-polymer covalent bond formed between the linker and a reactive group on the polymer, or by attaching a linker to the polymer and then attaching the active ingredient to the polymer-linker combination. The invention also provides a delivery system comprising an active ingredient covalently bonded through an acid-sensitive covalent bond to a linker which is in turn covalently bonded to a portion of subunits of a crosslinked polystyrene polymer. The invention further provides a method for treatment or prevention of gastric ulcers using a delivery system capable of delivering prostaglandin or prostacyclin drugs, especially misoprostol.

DETAILED DESCRIPTION OF THE INVENTION

Figure 1:
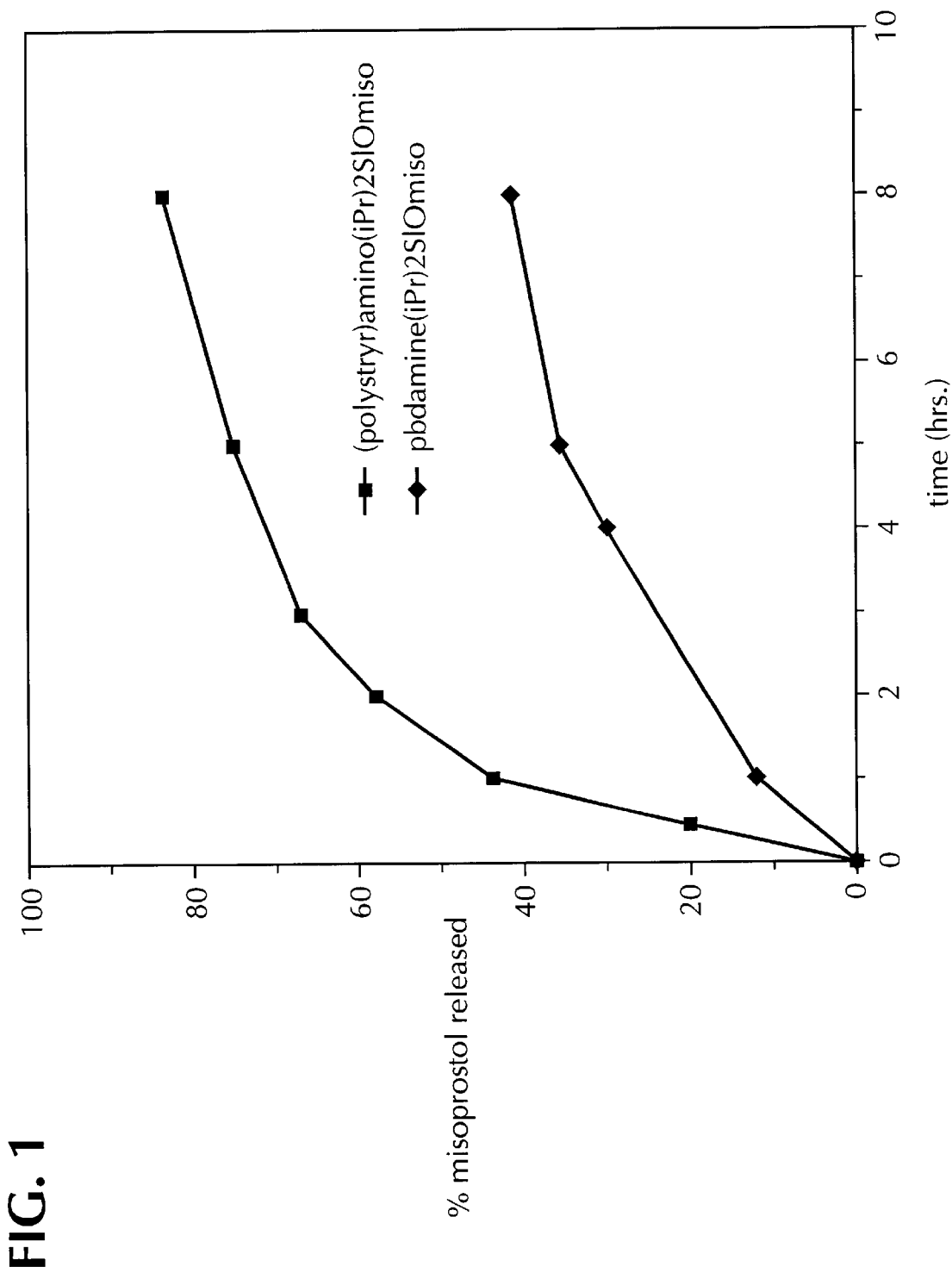
FIG. 1 is a graph illustrating the release performance at gastric pH of a polystyrene polymer substituted with misoprostol coupled to an acid-sensitive linker compared to an amine-functionalized polybutadiene substituted with the same misoprostol-linker combination.

The following terms used herein are defined. The term "THF" indicates the solvent tetrahydrofuran. The term "DMF" indicates the solvent N,N-dimethylformamide. The term "mercapto" refers to the substituent moiety SH, bonded through its sulfur atom to a carbon atom on a substrate. The term "alkyl" refers to a straight or branched alkyl group containing from 1 to 20 carbon atoms. The term "alkenyl" refers to a straight or branched hydrocarbon group containing from 1 to 20 carbon atoms and at least one carbon-carbon double bond. The term "alkynyl" refers to a straight or branched hydrocarbon group containing from 1 to 20 carbon atoms and at least one carbon-carbon triple bond. The term "cycloalkyl" refers to a cyclic alkyl group containing up to 20 carbon atoms. The term "aryl" refers to a group derived from a cyclic aromatic compound having up to 20 carbon atoms. The term "aralkyl" refers to an alkyl substituent substituted by an aryl group. The term "alkaryl" refers to an aryl substituent substituted by an alkyl group. The term "halo" means a fluoro, chloro, bromo, or iodo group. The term "subunit" refers to a portion of a polymer chain derived from a single molecule of monomer; subunits are often referred to in the art as "repeat units". A "styrenic" subunit is one derived from a monoethylenically unsaturated styrene monomer. Each type of subunit is repeated in the polymeric system depending on the initial composition of monomers used to produce the polymer.

In the pH-selective delivery system of this invention, the active ingredient is covalently bonded through an acid-sensitive covalent bond to a linker, which is in turn covalently bonded to a crosslinked polymeric resin. Attachment of the active ingredient by means of covalent bonds prevents release of active ingredient until conditions occur which will break the covalent bonds, and prevents continued release after these conditions cease to exist. When an acid-sensitive covalent bond formed with the linker is part of the delivery system, as in this invention, the active ingredient is released when the system is in an acidic medium, such as in the stomach.

The delivery system of this invention is based on a crosslinked polystyrene polymer. Preferred polystyrene polymers useful in this invention may be selected from the group consisting of poly[(4-halomethyl)styrene], poly[(3-halomethyl)styrene], mixtures of poly[(4-halomethyl) styrene] and poly[(3-halomethyl)styrene], poly[(4-dialkylaminomethyl)styrene], poly[(3-dialkylaminomethyl) styrene], and mixtures of poly[(4-dialkylaminomethyl) styrene] and poly[(3-dialkylaminomethyl)styrene]. The styrene subunits of the polystyrene polymers employed in this invention have a reactive group R substituted at the 3 or 4 position of the styrene aromatic ring. The R group is capable of forming a covalent bond by reaction with a reactive group on a linker. Particularly preferred R groups are dialkylaminomethyl groups or halomethyl groups, most preferably substituted at the 4 position of the styrene. The most preferred polymers are poly[(4-chloromethyl)styrene], poly[(3-chloromethyl)styrene], mixtures of poly[(4-chloromethyl)styrene] and poly[(3-chloromethyl)styrene], poly[(4-dimethylaminomethyl)styrene], poly[(3-dimethylaminomethyl)styrene], and mixtures of poly[(4-dimethylaminomethyl)styrene] and poly[(3-dimethylaminomethyl)styrene]. The preferred polymers are well known or may readily be prepared without undue experimentation. For example, in one procedure, they may be synthesized from a mixture of monomers containing the appropriate substituted styrene, preferably a 4-substituted styrene, and an amount of divinylbenzene suitable to produce the desired amount of crosslinking. Preferably, divinylbenzene is present in an amount ranging from 0.5% to 4% by weight, based on the total weight of monomers. Most preferably, the amount of divinylbenzene is about 2% by weight, based on the total weight of monomers. Another procedure for synthesizing poly[(4-chloromethyl)styrene], poly[(3-chloromethyl)styrene], or mixtures thereof, is to react a styrene-divinylbenzene copolymer with a chloromethylating complex according to the procedure described in European Patent Application 277,795, the disclosure of which is incorporated by reference herein.

When the polymer is a poly(haloalkyl substituted styrene), e.g., poly[(4-chloromethyl)styrene] or poly[(3-chloromethyl)styrene], a linker is used which contains a dialkylamino group which reacts with a portion of the haloalkyl groups, e.g., a 4-chloromethyl or 3-chloromethyl group, present on most of the polymer subunits to form a quaternary ammonium salt. The most preferred polymers if the linker contains a dialkylamino group are poly[(4-chloromethyl)styrene] and poly[(3-chloromethyl)styrene]. When the polymer is a poly(dialkylaminomethyl substituted styrene), e.g., poly[(4-dialkylaminomethyl)styrene] or poly[(3-dialkylaminomethyl)styrene], a linker is used which contains a haloalkyl group, e.g., a chloromethyl group, which reacts with a portion of the dialkylamino groups, e.g., 4-dialkylaminomethyl or 3-dialkylaminomethyl group, present on most. of the polymer subunits to form a quaternary ammonium salt. The most preferred polymers if the linker contains a chloromethyl group are poly[(4-dimethylaminomethyl)styrene] and poly[(3-dimethylaminomethyl)styrene].

The linker is a molecule with reactive substituents allowing it to be covalently bonded to both the active ingredient and the crosslinked polystyrene resin in such a way that an acid-sensitive compound is produced which will undergo cleavage at pH values lower than about 7 to release the active ingredient. The substituent which reacts with a functional group on the active ingredient forms a covalent bond which is acid-sensitive. This covalent bond will be cleaved in an acidic environment to release the active ingredient. Examples of such acid sensitive covalent bonds include silyl-ethers, silyl amines, silyl thioethers, vinyl silyl ethers, silyl esters, acetals, thioacetals, imines, aminals, carbonates, and vinyl ethers. A preferred acid-sensitive covalent bond is the silyl ether bond. The reactive substituent on the linker that reacts with the crosslinked polymer to covalently bond the linker to the polymer is any substituent which will form a nitrogen-carbon, oxygen-carbon, sulfur-carbon, or phosphorus-carbon bond with a polymer subunit, preferably a halo or dialkylamino substituent. Preferably, the linker is a compound having a silyl halide or silyl sulfonate ester substituent at one end of the molecule and a halo or dialkylamino substituent at the other end. The preferred linker has the structure

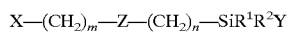

wherein X is halo or dialkylamino; Y is halo or an alkyl, haloalkyl, aryl, alkaryl, aralkyl, or haloaryl sulfonate ester; m is an integer from 0 to 2, inclusive; n is an integer from 0 to 3, inclusive;. Z is a divalent aryl, cycloalkyl, alkyl, alkenyl, or alkynyl group; and $R^1$ and $R^2$ are independently alkyl, aryl, cycloalkyl, alkenyl, alkynyl, alkaryl, or aralkyl. The $SiR^1R^2Y$ group, preferably a silyl chloride substituent, reacts with a hydroxyl, $CO_2H$, amino, mercapto, or enolizable carbonyl substituent on the active ingredient, forming a silyl ether, silyl ester, silyl amine, silyl thioether, or vinyl silyl ether bond, respectively.

Most preferably, the linker is a compound having the following structure:

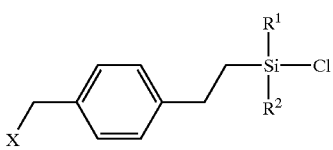

wherein X is halo or dialkylamino, and $R^1$ and $R^2$ are independently alkyl, aryl, cycloalkyl, alkenyl, alkynyl, alkaryl, or aralkyl. When X is a halo substituent, the linker forms a covalent bond with a poly(dialkylaminomethyl substituted styrene), e.g., poly[(4-dialkylaminomethyl) styrene] or poly[(3-dialkylaminomethyl)styrene], by alkylating the dialkylaminomethyl group to produce a quaternary ammonium salt. In this case, an alkyl halide is then optionally added to produce a quaternary ammonium salt at each unreacted dialkylaminomethyl substituent. In another embodiment, the polymer is treated first with an amount of alkyl halide sufficient to produce a quaternary ammonium salt on only a portion of the dialkylaminomethyl substituents, and then the linker is attached to substantially all of the remaining dialkylaminomethyl substituents. When X is a dialkylamino substituent, the linker forms a covalent bond with a poly(haloalkyl substituted styrene), e.g., poly[(4-chloromethyl)styrene] or poly[(3-chloromethyl)styrene], which alkylates the dialkylamino substituent to produce a quaternary ammonium salt. In this case, a trialkylamine is optionally added to produce a quaternary ammonium salt at each unreacted haloalkyl substituent. In another embodiment, the polymer is treated first with an amount of trialkylamine sufficient to produce a quaternary ammonium salt on only a portion of the haloalkyl substituents, and then the linker is attached to substantially all of the remaining haloalkyl substituents.

The active ingredient in this invention may be any substance that is desired for administration by selective release in an acidic environment, such as a drug, a seqeustrant, or a ligand for complexation of metals. In each case, a suitable active ingredient will be one which forms a pH-sensitive covalent bond with a reactive group on the linker. The active ingredient may be substituted by a hydroxyl, $CO_2H$, amino, mercapto, or enolizable carbonyl substituent group which is capable of reacting with a reactive group on the linker to form a covalent bond. Preferably, the active ingredient is a biologically active material, e.g., a drug, intended to be administered orally, especially those wherein gastric release, at a typical gastric pH value between 1 and 6, is preferred over intestinal release, or wherein control of the rate of release is desired for systemic action. For example, drugs for which delivery to the stomach is preferred include natural or synthetic prostaglandins and prostacyclins (e.g., misoprostol, enisoprost, enprostil, iloprost, and arbaprostil), any other drugs for treatment or prevention of peptic ulcers, gastric antisecretory drugs, antimicrobial drugs, prokinetic drugs, cytoprotective drugs and the like. Preferred prostaglandin drugs which may be delivered by the delivery system of this invention are those described in PCT Application No. WO 92/01477, the specification of which is incorporated herein. Exemplary antimicrobial drugs include tetracycline, metronidazole and erythromycin which can be used for the eradication of gastric microbes. The drug delivery system of this invention may be used to deliver more than one drug at a time, if there is a therapeutic need for simultaneous release of multiple drugs. The most preferred drug for delivery by the system of this invention is misoprostol. The amount of the active ingredient incorporated into the polymer depends on the desired amount of the particular active ingredient to be delivered. In general the amount of active ingredient is in the range from about 0.03% by weight to about 50% by weight of the polymeric delivery system, preferably in the range from about 0.05% by weight to about 20% by weight of the polymeric delivery system, and most preferably from 0.05% by weight to 2% by weight of the polymeric delivery system. In the case of misoprostol, the most preferred amount of misoprostol is about 1% by weight.

The preferred amount of delivery system to be administered is an amount that is sufficient to prevent, cure, or treat a condition for a desired period of time for which the delivery system of this invention is to be administered, and such an amount is referred to herein as "an effective amount". As is well known, particularly in the medicinal arts, effective amounts of medicinal agents vary with the particular agent employed, the condition being treated and the rate at which the composition containing the medicinal agent is eliminated from the body, as well as varying with the subject in which it is used, and the body weight of that subject. An effective amount is that amount which in a composition of this invention provides a sufficient amount of the active ingredient to provide the requisite activity of the active ingredient in the body of the treated subject for the desired period of time, and can be less than that amount usually used.

Inasmuch as amounts of particular active ingredients that are suitable for treating particular conditions are generally known, it is relatively easy to formulate a series of delivery systems containing a range of such active ingredients to determine the effective amount of such an active ingredient for a particular delivery system. Based upon a reading of the description herein and of the following examples, it is within the skill of the art to select an amount of any particular active ingredient and to covalently bond such an amount to a polymer herein described for delivering an effective amount of such an active ingredient. While the effective amount for all active ingredients cannot be stated, typical compositions of this invention may contain about one microgram to about one gram of active ingredient per dose administered. More preferably, a composition of this invention may contain about 1 microgram to about 250 milligrams per dose.

The method for preparing the delivery system of this invention comprises two steps. In one embodiment, the first step is attaching the active ingredient to a linker by forming an acid-sensitive covalent bond of one of the aforementioned types. The linker used in this embodiment may be a commercially available material with the aforementioned reactive groups or may be prepared without undue experimentation as described hereinafter. The active ingredient-linker combination is then attached to one of the aforementioned crosslinked polystyrene polymers by forming a covalent nitrogen-carbon, oxygen-carbon, sulfur-carbon, or phosphorus-carbon bond between the active ingredient-linker combination and a portion of the subunits of the polymer.

Another embodiment of the method for preparing the delivery system also comprises two steps. However, in this embodiment, the first step is attaching the linker to a portion of the subunits of one of the aforementioned crosslinked polystyrene polymers to form a covalent nitrogen-carbon, oxygen-carbon, sulfur-carbon, or phosphorus-carbon bond. The linker-polymer combination is then attached to the active ingredient by forming one of the aforementioned acid-sensitive covalent bonds.

In a particularly preferred embodiment of this invention, a preferred linker is prepared by introducing a silyl moiety into a carbon-carbon double bond in a substrate which also bears a reactive halo substituent. This is preferably accomplished by catalytic hydrosilylation of the substrate with a silane compound. In this case, suitable substrates for this reaction include those having both a carbon-carbon double bond, which can undergo hydrosilylation, and a reactive halo substituent, e.g., vinylbenzyl halides. The most preferred substrates are 3-vinylbenzyl chloride, 4-vinylbenzyl chloride, and mixtures thereof. Preferred silanes for use in this reaction include the dialkylsilanes and alkylarylsilanes, such as dimethylsilane, methylethylsilane, diethylsilane, methylisopropylsilane, ethylisopropylsilane, methylpropylsilane, ethylpropylsilane, diisopropylsilane, tert-butylmethylsilane, tert-butylethylsilane, tert-butylpropylsilane, isobutylisopropylsilane, isobutylethylsilane, methylphenylsilane, ethylphenylsilane, isopropylphenylsilane, and the like. The most preferred silanes are diisopropylsilane, tert-butylmethylsilane, and tert-butylethylsilane. Preferred catalysts for promoting the hydrosilylation reaction include a variety of platinum and rhodium catalysts, such as platinum divinyltetramethyldisiloxane and tris(triphenylphosphine)rhodium(I) chloride ("Wilkinson's catalyst"). The most preferred catalyst is platinum divinyltetramethyldisiloxane. Preferred solvents for use in hydrosilylation include any solvent which will dissolve the substrate and which will not itself undergo hydrosilylation. Examples are the aromatic hydrocarbon solvents such as toluene, any of the xylenes, and ethylbenzene, and aliphatic hydrocarbon solvents such as any of the hexanes, heptanes, octanes, cyclohexane, cyclopentane, and the like, and mixtures thereof. The most preferred solvents are toluene and the xylenes, and mixtures thereof. The hydrosilylation reaction is preferably carried out at a temperature in the range from about 15° C. to about 120° C., most preferably from 50° C. to 80° C. Preferably, the reaction is allowed to proceed for a period of about 1 to about 24 hours, most preferably from 5 to 14 hours.

The second step in preparation of a preferred linker employed in this invention is chlorination of the silane product produced by the hydrosilylation reaction described above. This is typically accomplished by treatment with a solution of chlorine gas in an organic solvent. Suitable solvents for this reaction include the halogenated solvents, such as chlorobenzene, 1,2-dichlorobenzene, dichloromethane, tetrachloromethane, chloroform, 1,2-dichloroethane, 1,1,1-trichloroethane, 1,1,2,2-tetrachloroethane, and the like. Preferred solvents are dichloromethane, 1,2-dichloroethane, and tetrachloromethane. The most preferred solvent is dichloromethane. The chlorination is typically carried out at a temperature below room temperature, preferably below about −20° C., most preferably at about −78° C. Preferably, the reaction is allowed to proceed for a period of about 10 minutes to about 3 hours. The reaction mixture may be monitored using an analytical method capable of detecting the level of starting material, product, or both, e.g., gas chromatography. The reaction is typically allowed to proceed until analysis indicates that the starting material is substantially consumed.

Preparation of an active ingredient-linker combination is accomplished in a preferred embodiment of this invention by coupling the active ingredient to the linker, typically by combining the drug and the silyl chloride produced in the chlorination step described above. Suitable solvents for this step include those which are capable of dissolving the drug, but which are not reactive towards the silyl chloride functional group, including the polar aprotic solvents, such as N,N-dimethylformamide (DMF), THF, N,N-dimethylacetamide, N-methylpyrrolidone, 1,2-dimethoxyethane, and halogenated solvents such as chlorobenzene, 1,2-dichlorobenzene, dichloromethane, tetrachloromethane, chloroform, 1,2-dichloroethane, 1,1,1-trichloroethane, 1,1,2,2-tetrachloroethane, and the like. Preferred solvents are DMF, dichloromethane, and THF. The most preferred solvent is DMF. An additional compound may be added as a promoter for the coupling reaction. Preferred promoters include imidazole and 4-dimethylaminopyridine. The most preferred promoter is imidazole. This reaction is preferably carried out at a temperature in the range from about 15° C. to about 100° C., most preferably from 20° C. to 40° C. Preferably, the reaction is allowed to proceed for a period of about 1 to about 18 hours. The progress of the reaction may be followed by using a method capable of detecting the level of starting material, product, or both, such as thin-layer chromatography or liquid chromatography. The reaction is typically allowed to proceed until analysis indicates that the starting material is substantially consumed.

In one embodiment of the method of this invention, following the preparation of an active ingredient-linker combination, the active ingredient-linker combination is coupled to a crosslinked polystyrene resin, e.g., poly[(4-dialkylaminomethyl)styrene] or poly[(3-dialkylaminomethyl)styrene] resin, to form the active ingredient delivery system. In a preferred embodiment of this invention, a crosslinked poly[(4-chloromethyl)styrene] or poly[(3-chloromethyl)styrene], or a mixture thereof is first combined with a dialkylamine in a solvent to produce a poly[(4-dialkylaminomethyl)styrene] or poly[(3-dialkylaminomethyl)styrene], or a mixture thereof.

Suitable crosslinked poly[(4-chloromethyl)styrene] or poly[(3-chloromethyl)styrene] resins are commercially available resins, including those manufactured by Purolite International Limited, Mid Glamorgan, Wales. The most preferred resin is one made with a divinylbenzene monomer content of about 2% by weight. Suitable dialkylamines include dimethylamine, methylethylamine, diethylamine, methylpropylamine, methylbutylamine, methylisopropylamine, ethylpropylamine, and the like. The most preferred dialkylamine is dimethylamine. Solvents which are suitable for this reaction include tetrahydrofuran (THF), ethyl acetate, dichloromethane, toluene, alcoholic solvents, and water, and mixtures thereof. The preferred solvents are THF, ethyl acetate and dichloromethane. The most preferred solvent is THF. The delivery system is then prepared by combining the active ingredient-linker combination and the crosslinked polymeric resin in a solvent. Suitable solvents for this step include those which are polar and capable of swelling the crosslinked polymeric resin sufficiently to allow for rapid reaction with the active ingredient-linker combination. Examples of such solvents include tetrahydrofuran (THF), N,N-dimethylformamide (DMF), ethyl acetate, and dichloromethane. The most preferred solvent is THF. An iodide salt may be added to promote the reaction. Suitable iodide salts include tetrabutylammonium iodide, tetrapropylammonium iodide, tetraethylammonium iodide, tetramethylammonium iodide, potassium iodide, sodium iodide, cesium iodide, and the like. Preferred iodide salts include tetrabutylammonium iodide and potassium iodide. The most preferred salt is tetrabutylammonium iodide. This reaction is typically carried out at a temperature in the range from about 15° C. to about 100° C., most preferably from 25° C. to 40° C. Preferably, the reaction is allowed to proceed for a period of about 5 to about 18 hours. The progress of the reaction may be followed by using a method capable of detecting the level of starting material, product, or both, e.g., thin-layer or liquid chromatography. The reaction is typically allowed to proceed until the starting material is substantially consumed. After the reaction period, the resin is isolated.

The resin is preferably then reacted with an alkyl halide to alkylate substantially all of the remaining dialkylamino groups on the resin. Suitable alkyl halides for this purpose include methyl chloride, ethyl chloride, propyl chloride, isopropyl chloride, butyl chloride, and the like. The most preferred alkyl halide is methyl chloride. This reaction is typically carried out at a temperature in the range from about 10° C. to about 50° C., most preferably from about 15° C. to about 30° C. Preferably, the reaction is allowed to proceed for a period of about 1 hour to about 3 days, most preferably from 2 to 3 days.

In another embodiment of this invention, the alkyl halide is added to the crosslinked poly(dialkylaminomethyl substituted styrene) in an amount sufficient to produce a quaternary ammonium salt at only a portion of the subunits, and then the active ingredient-linker combination is attached to the remaining dialkylamino groups.

In another preferred embodiment of this invention, the aforementioned active ingredient-linker combination, which bears a chloromethyl group is treated with a dialkylamine in a solvent to produce the active ingredient-dialkylamino-substituted linker combination. Suitable dialkylamines for this reaction include dimethylamine, methylethylamine, diethylamine, methylpropylamine, methylbutylamine, methylisopropylamine, ethylpropylamine, and the like. The most preferred dialkylamine is dimethylamine. The amine is added in an amount ranging from 1 to 30 equivalents based on the amount of active ingredient-linker combination, preferably from about 1 to about 2 equivalents. Suitable solvents for this reaction include THF, dichloromethane, ethyl acetate, 1,2-dichloroethane, toluene, xylenes, diethyl ether, N,N-dimethylformamide, N,N-dimethylacetamide, N-methylpyrrolidone, and 1,2-dimethoxyethane. The preferred solvents are THF and dichloromethane, and the most preferred solvent is THF. The reaction temperature for this step is suitably in the range from about 0° C. to about 100° C., preferably in the range from about 20° C. to about 40° C., and most preferably at about 25° C. The reaction time varies from about 3 hours to about 24 hours, depending on the identity of the amine and the solvent. This dialkylamino-substituted linker-active ingredient combination is then reacted with one of the aforementioned suitable crosslinked poly(haloalkyl substituted styrene) polymers, e.g., poly[(4-chloromethyl)styrene] or poly[(3-chloromethyl)styrene], to form the active ingredient delivery system. In a preferred embodiment of this invention, poly[(4-chloromethyl) styrene], poly[(3-chloromethyl)styrene], or a mixture thereof, is combined with the dialkylamino-substituted linker-active ingredient combination in a solvent. Suitable solvents for this step include those which are polar and capable of swelling the crosslinked polymeric resin sufficiently to allow for rapid reaction with the active ingredient-linker combination. Examples of such solvents include tetrahydrofuran (THF), N,N-dimethylformamide (DMF), ethyl acetate, and dichloromethane. The most preferred solvent is THF.

An iodide salt may be added to promote the reaction. Suitable iodide salts include tetrabutylammonium iodide, tetrapropylammonium iodide, tetraethylammonium iodide, tetramethylammonium iodide, potassium iodide, sodium iodide, cesium iodide, and the like. Preferred iodide salts include tetrabutylammonium iodide and potassium iodide. The most preferred salt is tetrabutylammonium iodide. This reaction is typically carried out at a temperature in the range from about 15° C. to about 100° C., most preferably from 25° C. to 40° C. Preferably, the reaction is allowed to proceed for a period of about 5 to about 18 hours. The progress of the reaction may be followed by using a method capable of detecting the level of starting material, product, or both, e.g., thin-layer or liquid chromatography. The reaction is typically allowed to proceed until the starting material is substantially consumed. After the reaction period, the resin is isolated.

The resin is preferably then reacted with a trialkylamine to form a quaternary ammonium salt on substantially all of the remaining chloromethyl groups on the resin. Suitable trialkylamines for this reaction include trimethylamine, dimethylethylamine, diethylmethylamine, dimethylpropylamine, dimethylbutylamine, triethylamine, dimethylisopropylamine, diethylpropylamine, and the like. The most preferred trialkylamine is trimethylamine. This reaction is typically carried out at a temperature in the range from about 10° C. to about 50° C., most preferably from about 15° C. to about 30° C. Preferably, the reaction is allowed to proceed for a period of about 1 hour to about 3 days, most preferably from 2 to 3 days.

In another embodiment of this invention, the trialkylamine is added to the crosslinked poly(haloalkyl substituted styrene) in an amount sufficient to produce a quaternary ammonium salt at only a portion of the subunits, and then the active ingredient-linker combination is attached to the remaining haloalkyl groups.

The examples which follow are intended as an illustration of certain preferred embodiments of the invention, and no limitation of the invention is implied.

EXAMPLE 1

Preparation of Crosslinked Poly[(4-dimethylaminomethyl)styrene]

Purolite resin D-3196 AGD:16:44 (50 g, Purolite International Limited, Mid Glamorgan, Wales), a crosslinked poly[(4-chloromethyl)styrene], was stirred for about 30 minutes in each of the following solutions, then filtered to remove the solution: deionized water (500 ml), 10% HCl solution (500 ml), deionized water (500 ml), THF (HPLC grade, two 500 ml portions), THF (anhydrous, inhibitor-free, two 500 ml portions). The resin was then extracted for 72 hours with anhydrous, inhibitor-free THF (1200 ml) in a soxhlet apparatus. The cleaned resin was dried overnight under high vacuum, and was then combined with a solution of dimethylamine in THF (2M solution, 103 g, 7 eq) and allowed to react overnight at room temperature, and then overnight at reflux. The product resin is cleaned by stirring for about 30 minutes in each of the following solutions, followed by filtration to remove the solution: THF (HPLC grade, 500 ml), deionized water (four 1 liter portions), THF (HPLC grade, 500 ml), THF (HPLC grade, two 1 liter portions), THF (anhydrous, inhibitor-free, two 1 liter portions). The resin was then dried overnight at room temperature followed by drying overnight over $P_2O_5$ at 75° C.

EXAMPLE 2

Preparation of Misoprostol-Linker Combination
(a) Hydrosilylation of p-vinylbenzyl chloride with diisopropylsilane.

Under a nitrogen atmosphere a 250 ml round-bottom flask was charged with p-vinylbenzyl chloride (31 g, 0.20 mol), diisopropylsilane (24 g, 0.20 mol), a solution of platinum divinyltetramethyldisiloxane in xylene (2.3% solution, 14 g), and toluene (25 ml). After stirring for one hour at room temperature, the reaction mixture was heated to 70° C. and stirred for 14 hours. After removing the toluene with a rotary evaporator, the residue was redissolved in hexane and filtered to remove insoluble impurities. The hexane was then evaporated, leaving a residue which was purified by elution from silica gel with hexane. Pure 1-diisopropylsilyl-2-[(4-chloromethyl)phenyl]ethane was obtained from the hexane eluent (40 g, 71% yield).

(b) Chlorination of the product from step (a).

The product of part (a) (30 g) was dissolved in dichloromethane (25 ml) and cooled to −78° C. A solution of chlorine gas in dichloromethane was slowly added to the solution at −78° C. until analysis by gas chromatography showed that all of the silane was converted to product. Removal of chlorine with a nitrogen sweep, followed by evaporation of solvent gave 1-diisopropylchlorosilyl-2-[(4-chloromethyl)phenyl]ethane of greater than 95% purity.

(c) Coupling of misoprostol to the linker.

Misoprostol (0.5 g, 1.3 mmol) was dissolved in dry DMF (2 ml) and then imidazole (0.175 g, 2.0 mmol) in DMF (2 ml) was added. After addition of 1-diisopropylchlorosilyl-2-[(4-chloromethyl)phenyl]ethane (0.385 g, 1.4 mmol), the reaction mixture was stirred at room temperature for 14 hours. The coupled product was isolated by means of silica gel chromatography using ethyl acetate as an eluent to obtain 0.51 g (60%). The product has the structure shown below:

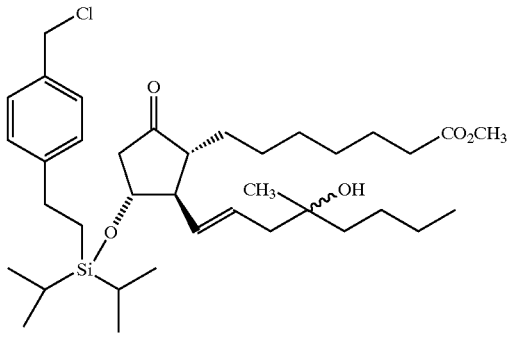

EXAMPLE 3

Preparation of Misoprostol Delivery System

The misoprostol-linker combination (40.5 mg) was combined with the resin product of Example 1 (2.38 g) and tetrabutylammonium iodide (23 mg) in THF (11 g) and maintained at 40° C. for 72 hours. After washing the resin with THF (1 liter), methyl chloride (20% by volume in 40 g THF) is added and allowed to react at room temperature for 64 hours. After filtration to remove solvent, 3.0 g of resin product was obtained. Analysis indicated a bound misoprostol concentration of 0.52 mg misoprostol/100 mg resin. At pH 1.4 (room temperature), 20% release of misoprostol was observed in 30 minutes and 75% in 5 hours. No misoprostol release occurred at pH 5 (room temperature).

The in vitro release rate of misoprostol from this delivery system at a pH value of 1.4 was measured as follows. Samples of the delivery system (10 mg) were weighed into a centrifuge tube with a stir bar, then aqueous HCl solution (0.01 N, 1.5 ml) and methanol (HPLC grade, 1.5 ml) were added to the tube. The reaction was allowed to proceed for a sufficient time to obtain maximum release of the drug from the matrix. HPLC analysis was carried out on a Spectra-Physics HPLC fitted with an Altex/Beckman Ultrasphere ODS 5 $\mu$m, 80 angstrom pore size, 4.6 mm×25 cm, reverse-phase column. Samples were injected using a Spectra-Physics autosampler set to a 100 $\mu$l injection size. Samples were eluted with a ternary solvent system of water, methanol, and acetonitrile using an SP8500 dynamic mixer. All solvents used were HPLC grade. Samples were detected with a UV detector set to a wavelength of 210 nm, AUFS= 0.100, and rise time=1.00. The percent release was then obtained at each time point from the following equation:

$$\% \text{ release at time } t = 100 \times \frac{[\text{conc. of misoprostol}]_t}{[\text{conc. of misoprostol}]_{max}}$$

The release rate was compared to that of a polybutadiene-amine system using the same linker, and prepared as described in PCT Application No. WO 92/01477. As shown in FIG. 1, the release rate of this delivery system of this example at one hour is about four times greater than that of the polybutadiene system.

EXAMPLE 4

Reaction of Dialkylamino Linker with Chloromethyl Polymer (Alternative Preparation of Misoprostol Delivery System)

(a) Preparation of dialkylamino linker.

The product from Example 2(c) (20.3 mg) and dimethylamine (2M in THF, 55 mg) were placed in a 5 ml vial and kept at room temperature for 18 hours. The mixture was extracted with three 2 ml portions of diethyl ether, the combined extracts filtered, and the filtrate evaporated under high vacuum to yield the product (20.3 mg).

(b) Preparation of misoprostol delivery system.

Crosslinked poly[(4-chloromethyl)styrene] resin (obtained from Purolite, International Limited, Mid Glamorgan, Wales) (101 mg) was added to a solution of the product from step (a) (18.1 mg) in anhydrous THF (434 mg). The mixture was kept at room temperature for 96 hours. The resin was washed with six 2.8 g portions of THF, then treated with a solution of trimethylamine in THF (0.984 mmol/g, 2.9 g). After three hours, the mixture was evaporated to dryness. Elemental analysis indicated that 82.5% quaternization of the chloromethyl groups had been achieved. A sodium methoxide assay was carried out according to the following procedure. The delivery system (50 mg) was stirred in methanol (2.5 ml) and methanolic sodium methoxide (25% solution, 0.5 ml) for 15 minutes at 25° C. An aliquot was analyzed by reverse-phase HPLC with a detection wavelength of 280 nm. The only product observed was the PGB derivative of misoprostol, methyl 11-[[butylbis(1-methylethyl)silyl]oxy]-16-hydroxy-16-methyl-9-oxo-prost-13-en-l-oic acid. The HPLC results indicated that the drug loading on the final resin was 4% by weight, and that the loading after 25 hours was 2% by weight.

Other variations and modifications of this invention will be obvious to those skilled in the art. This invention is not limited except as set forth in the claims.

What is claimed is:

1. A delivery system comprising: an active ingredient covalently bonded to a linker through an acid-sensitive covalent bond formed with a hydroxyl, $CO_2H$, amino, mercapto, or enolizable carbonyl moiety of the active ingredient, said linker being covalently bonded to a portion of styrenic subunits of a crosslinked polystyrene polymer through a linker-polymer covalent bond selected from the group consisting of a nitrogen-carbon bond and a phosphorus-carbon bond, wherein the crosslinked polystyrene polymer is selected from the group consisting of poly[(4-dialkylaminomethyl)styrene], poly[(3-dialkylaminomethyl)styrene], and mixtures of poly[(4-dialkylaminomethyl)styrene] and poly[(3-dialkylaminomethyl)styrene].

2. The delivery system of claim 1 wherein the crosslinked polymer is poly[(4-dimethylaminomethyl)styrene], poly[(3-dimethylaminomethyl)styrene], or a mixture thereof.

3. The delivery system of claim 2 wherein substantially all styrenic subunits of the crosslinked polystyrene polymer not bonded to the linker are substituted by quaternary ammonium salt moieties.

4. The delivery system of claim 3 wherein the active ingredient and the linker form a substituent on a 4-dimethylaminomethyl moiety or a 3-dimethylaminomethyl moiety having a structure represented by

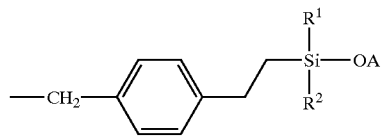

wherein OA is the covalently bonded active ingredient; and $R^1$ and $R^2$ are independently alkyl, aryl, cycloalkyl, alkenyl, alkynyl, alkaryl, or aralkyl.

5. The delivery system of claim 4 wherein the covalently bonded active ingredient —OA is derived from a natural or synthetic prostaglandin or prostacyclin.

6. The delivery system of claim 5 wherein $R^1$ and $R^2$ are isopropyl.

7. The delivery system of claim 5 wherein $R^1$ is tertiary butyl and $R^2$ is methyl.

8. The delivery system of claim 5 wherein $R^1$ is tertiary butyl and $R^2$ is ethyl.

9. The delivery system of claims 6, 7, or 8 wherein the covalently bonded active ingredient is derived from misoprostol.

10. A method of treatment for gastric ulcers comprising administering the delivery system of claim 5 to a human suffering therefrom.

11. A method for prevention of gastric ulcers comprising administering the delivery system of claim 5 to a human.

12. A method of treatment for gastric ulcers comprising administering the delivery system of claim 9 to a human suffering therefrom.

13. A method for prevention of gastric ulcers comprising administering the delivery system of claim 9 to a human.

* * * * *

UNITED STATES PATENT AND TRADEMARK OFFICE
CERTIFICATE OF CORRECTION

PATENT NO. : 6,471,955 B1
DATED : October 29, 2002
INVENTOR(S) : Samuel J. Tremont et al.

It is certified that error appears in the above-identified patent and that said Letters Patent is hereby corrected as shown below:

Drawings,
Figure 1,
"(polystryr)amino(iPr)2SIOmiso" should read --(polystryr)amine(iPr)2SiOmiso-- ; and "pbdamine(iPr)2SIOmiso" should read --pbdamine(iPr)2SiOmiso--.

Column 1,
Line 52, "olymer" should read -- polymer --; and
Line 53, "rug" should read -- drug --.

Column 4,
Line 29, "most." should read -- most --;
Line 43, "acid sensitive" should read -- acid-sensitive --; and
Line 63, "inclusive;." should read -- inclusive; --.

Column 12,
Line 15, "$\% \text{ release at time } t = 100 x \frac{[conc. of\ misoprostol]_1}{[conc. of\ miscoprostol]_{max}}$"

should read -- $\% \text{ release at time } t = 100 x \frac{[conc. of\ misoprostol]_t}{[conc. of\ miscoprostol]_{max}}$ --.

Signed and Sealed this

Fifteenth Day of July, 2003

JAMES E. ROGAN
*Director of the United States Patent and Trademark Office*